US011259955B2

(12) United States Patent
Singh

(10) Patent No.: US 11,259,955 B2
(45) Date of Patent: Mar. 1, 2022

(54) APPARATUS AND METHODS TO CONVERT DENTAL, ORAL, ORTHODONTIC APPLIANCES, RETAINERS, AND DENTURES INTO A MULTIFUNCTIONAL ORAL APPLIANCE

(71) Applicant: Pankaj Pal Singh, Brookville, NY (US)

(72) Inventor: Pankaj Pal Singh, Brookville, NY (US)

( * ) Notice: Subject to any disclaimer, the term of this patent is extended or adjusted under 35 U.S.C. 154(b) by 177 days.

(21) Appl. No.: 16/424,771

(22) Filed: May 29, 2019

(65) Prior Publication Data

US 2020/0375789 A1 Dec. 3, 2020

(51) Int. Cl.
*A61F 5/56* (2006.01)
*A61C 7/36* (2006.01)
*A61C 7/08* (2006.01)

(52) U.S. Cl.
CPC ............... *A61F 5/566* (2013.01); *A61C 7/08* (2013.01); *A61C 7/36* (2013.01)

(58) Field of Classification Search
CPC ............... A61F 5/56–566; A61F 5/058; A61F 5/05883; A61F 5/05891; A61F 2005/563; A61C 7/08; A61C 7/36; A61C 7/00; A61C 5/007
See application file for complete search history.

(56) References Cited

U.S. PATENT DOCUMENTS

| | | | |
|---|---|---|---|
| 5,868,138 A | 2/1999 | Halstrom | |
| 6,325,064 B1 | 12/2001 | Thornton | |
| 6,418,933 B1 | 7/2002 | Strong | |
| 6,983,752 B2 | 1/2006 | Garabadian | |
| 7,146,982 B2 * | 12/2006 | Mousselon | A61F 5/566 128/848 |
| 7,354,270 B2 * | 4/2008 | Abolfathi | A61C 7/08 433/215 |
| D685,098 S | 6/2013 | Tompkins | |
| D720,858 S | 1/2015 | Burton | |
| 9,393,085 B2 * | 7/2016 | Mohr | A61C 7/36 |
| 9,615,964 B2 | 4/2017 | Rogers | |
| 9,814,546 B2 | 11/2017 | Shatkin | |
| 2008/0072915 A1 | 3/2008 | Nelissen | |
| 2009/0036889 A1 | 2/2009 | Callender | |
| 2010/0095970 A1 | 4/2010 | Katz et al. | |
| 2011/0155144 A1 * | 6/2011 | Tousssaint | A61F 5/566 128/848 |
| 2012/0199136 A1 | 8/2012 | Urbano | |

(Continued)

FOREIGN PATENT DOCUMENTS

EP 2143397 A1 * 1/2010 ............... A61C 7/08

*Primary Examiner* — Michelle J Lee

(74) *Attorney, Agent, or Firm* — Dunlap Bennett & Ludwig, PLLC; Brendan E. Squire

(57) ABSTRACT

An apparatus and method to convert a dental, oral, orthodontic appliances, retainers, and dentures into a multifunctional oral appliance. The apparatus includes plurality of mechanical connectors and attachments made of plastic, ceramic, or metal, that convert any dental or oral appliances, into multipurpose, three dimensionally adjustable oral appliances for treating obstructive sleep apnea, snoring, temporomandibular joint and musculoskeletal disorders of the jaw, and for improving breathing from the mouth even when nasal passages are blocked.

4 Claims, 4 Drawing Sheets

(56) References Cited

U.S. PATENT DOCUMENTS

2014/0020691 A1* 1/2014 Sweeney ............... A61F 5/566
                                                    128/848
2015/0216716 A1   8/2015 Aldecoa
2017/0216084 A1   8/2017 Veis

* cited by examiner

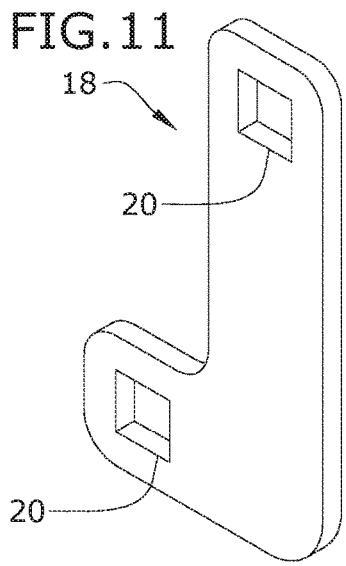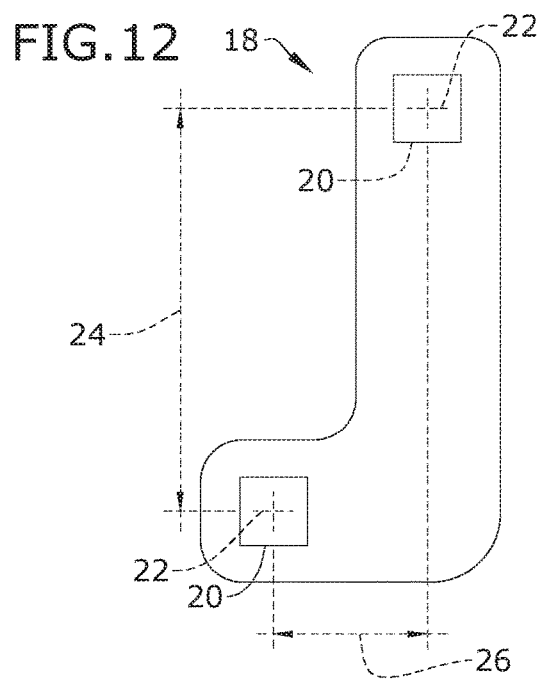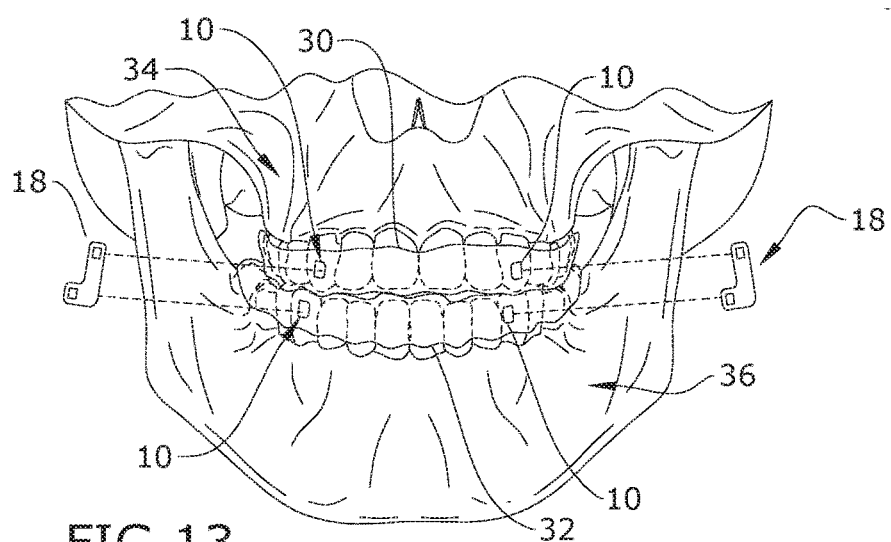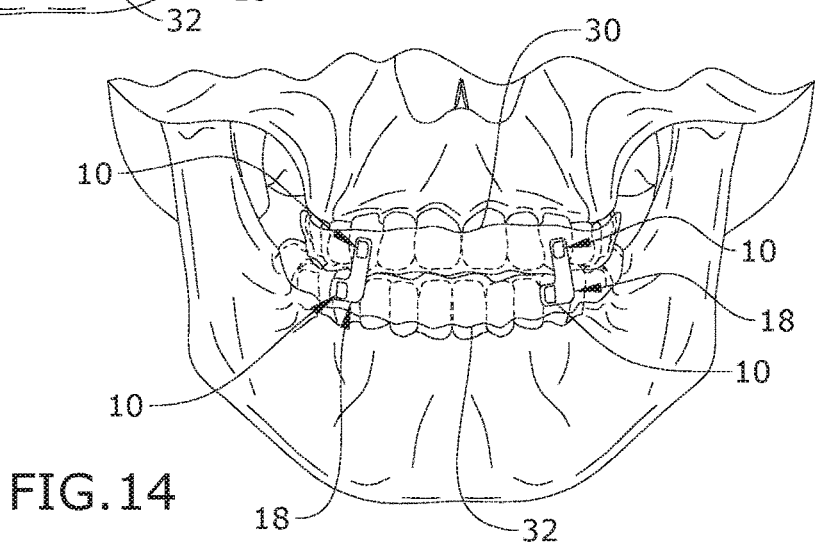

APPARATUS AND METHODS TO CONVERT DENTAL, ORAL, ORTHODONTIC APPLIANCES, RETAINERS, AND DENTURES INTO A MULTIFUNCTIONAL ORAL APPLIANCE

BACKGROUND OF THE INVENTION

The current invention relates to oral appliances, and more particularly to an attachment and connector that converts dental, oral, orthodontic appliances, retainers, and dentures into a multifunctional oral appliance.

One out of four adults and up to 10% of children suffer from obstructive sleep apnea. Further, patients with few teeth or no teeth, wearing dentures, in active orthodontic therapy, and with limited mouth opening are just a few of the many that cannot be treated simultaneously with oral appliances used for treatment of obstructive sleep apnea, snoring, and temporomandibular joint and musculoskeletal disorders of the jaw. Therefore, a significant majority of those that need treatment go untreated.

Most all-custom oral appliances used for treatment of obstructive sleep apnea, snoring, and temporomandibular joint and musculoskeletal disorders of the jaw have been scientifically proven to have inadequate long-term compliance due to poor fit and comfort. In addition, most all custom oral appliances used for treatment of obstructive sleep apnea, snoring, and temporomandibular joint and musculoskeletal disorders of the jaw are only adjustable longitudinally in one dimension only. If the therapy has been shown to be ineffective, and a vertical or lateral positioning of the custom oral appliance is to be made, then it requires that a new custom oral appliance be fabricated in the new therapeutic position.

The first limitation of all dental, oral and orthodontic appliances is that they treat a singular condition at a time. The second limitation is that almost all custom oral appliances be manufactured in a dental laboratory. The third limitation of oral appliances that are used to treat obstructive sleep apnea, snoring, and temporomandibular joint and musculoskeletal disorders of the jaws is that they are only adjustable along the x axis, one dimensionally.

There exists a need for a single device that can simultaneously and three dimensionally offer effective treatment of obstructive sleep apnea, snoring and temporomandibular joint and musculoskeletal disorders of the jaw.

SUMMARY OF THE INVENTION

In one aspect of the present invention, a dental appliance is disclosed. The dental appliance includes a maxillary appliance fitted to a maxillary dental structure of a patient. A mandibular appliance is also fitted to a mandibular dental structure of the patient. An attachment piece having a base, a head disposed at a distal end and a constriction intermediate the base and the head. The base of the attachment piece is affixed to each of the maxillary appliance and the mandibular dental appliance on a left side and a right side thereof. A titration connector, having a first opening on a proximal end is configured to fit onto the attachment piece of the maxillary appliance, and a second opening on a distal end configured to fit on the attachment piece of the mandibular appliance.

The spacing between the first opening and the second opening is selected for a desired offset dimension between the maxillary appliance and the mandibular appliance. The desired offset may include a vertical dimension between connector openings. The desired offset may also include a horizontal dimension between connector openings. The desired offset may also include a lateral offset dimension.

In some embodiments, the titration connector is an elongate plate. In other embodiments the titration connector is an L-shaped plate. In yet other embodiments, the titration connector comprises a triangular shaped plate.

In other embodiments, a keyed slot is defined in a surface of the plate. The keyed slot is configured to adjustably receive the attachment piece. A locking element is configured to attach to the head of the attachment piece and retain the attachment piece at a desired position within the keyed slot.

In some embodiments, the keyed slot may include an origin dimensioned to receive the head of the connector and a vertical extension dimensioned to receive the constriction of the connector. In other embodiments, the keyed slot includes an origin dimensioned to receive the head of the connector and a horizontal extension dimensioned to receive the constriction of the connector.

Other aspects of the invention include a kit for adapting a dental appliance into a multifunctional oral appliance. The kit includes an attachment piece having a base at a proximal end configured to be affixed to an outer surface of the dental appliance, a head at a distal end, and a constriction intermediate the base and the head. A titration connector formed as a flat plate has a plurality of titration connector openings dimensioned to be captively received in the constriction and retained by the head of the attachment piece The titration connector openings are disposed at a predetermined vertical separation dimension (CPV) and a predetermined anterior-posterior dimension (CPAP) 26. The titration connector may be formed as an L-shaped plate, in which one of the plurality of titration connector openings is disposed on the base of the L and a second of the plurality of titration connector openings is positioned on the leg of the titration connector.

Another aspect of the invention includes a method of adapting a dental appliance into a multifunctional oral appliance. The method includes affixing an attachment piece having a base at a proximal end, a head at a distal end, and a constriction intermediate the base and the head to each of a maxillary dental appliance and a mandibular dental appliance. The method also includes applying a titration connector between the attachment piece of the maxillary dental appliance and the mandibular dental appliance, the titration connector having a plurality of titration connector openings dimensioned to be captively received in the constriction and retained by the head of the attachment piece.

In some embodiments, the method includes disposing the titration connector openings at a predetermined vertical separation dimension (CPV). Other embodiments of the method include disposing the titration connector openings at a predetermined anterior-posterior dimension (CPAP).

These and other features, aspects and advantages of the present invention will become better understood with reference to the following drawings, description and claims.

BRIEF DESCRIPTION OF THE DRAWINGS

FIG. 11 is a perspective view of an invention component 18 titration connector with a non-zero 30 titration vertical dimension (V) (CPV-4 mm);

FIG. 12 is a front view of an invention component 18 titration connector with a non-zero 30 titration vertical dimension (V) (CPV-4 mm);

FIG. 13 is an exploded view of an invention component 18 titration connector with a non-zero 30 titration vertical dimension (V) (CPV-4 mm) demonstrating the attachment phase of the invention in an exemplary configuration;

FIG. 14 is an exploded view of an invention component 18 titration connector with a non-zero 30 titration vertical dimension (V) (CPV-4 mm) demonstrated post attachment phase of the invention in an exemplary configuration;

DETAILED DESCRIPTION OF THE INVENTION

Figure 1:
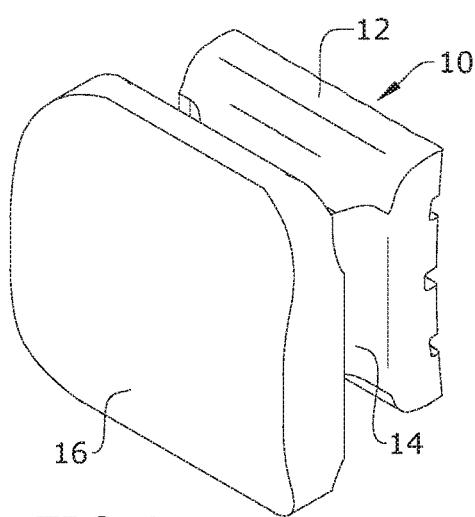
FIG. 1 is a perspective view of an invention component 10 attachment.
Figure 2:
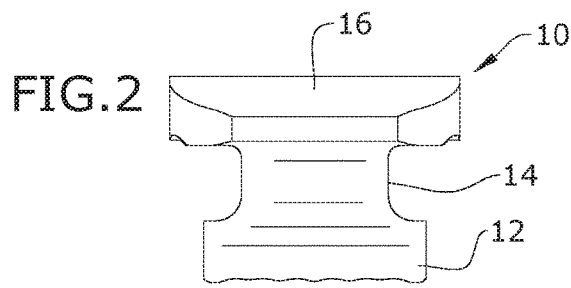
FIG. 2 is a top view of an invention component 10 attachment.
Figure 3:
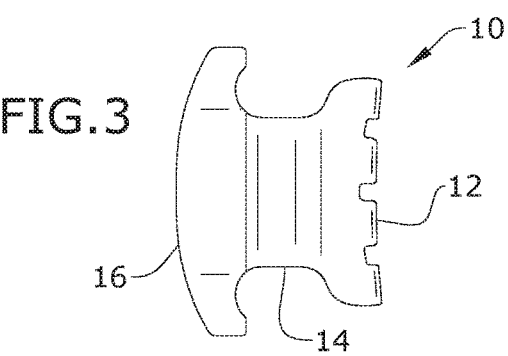
FIG. 3 is a side view of an invention component 10 attachment.
Figure 4:
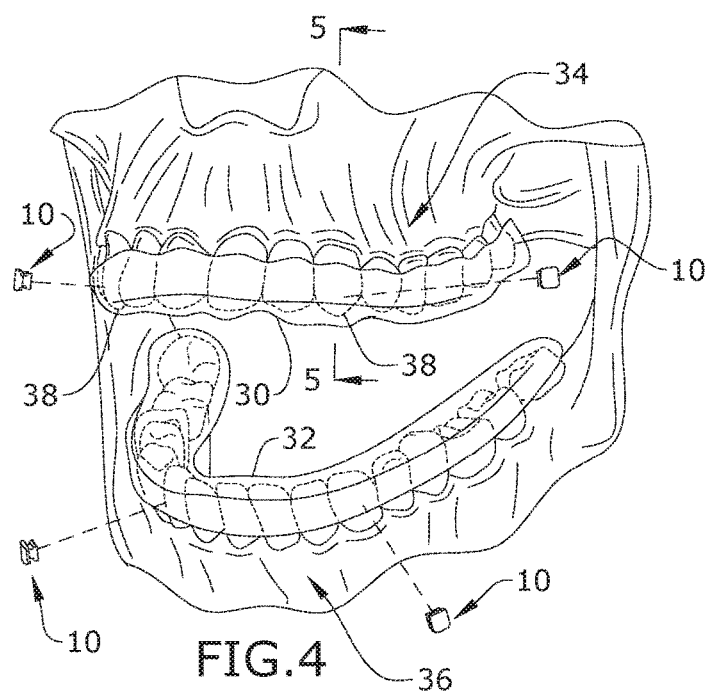
FIG. 4 is an exploded view demonstrating the attachment phase of the invention in an exemplary configuration.
Figure 5:
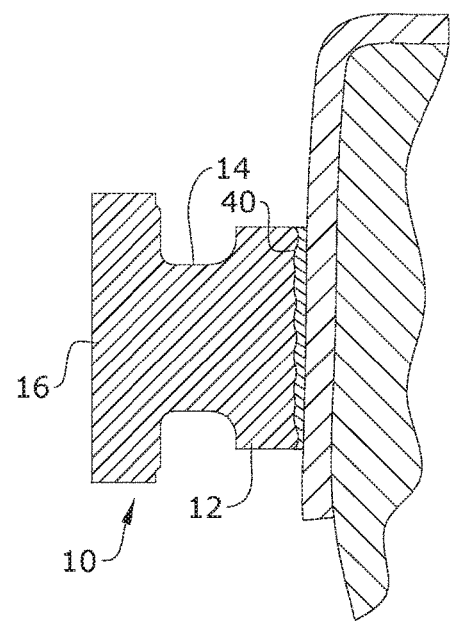
FIG. 5 is a section view of the invention taken along line 5-5 in FIG. 4. shown post-attachment.

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

As stated, most all custom oral appliances used for treatment of obstructive sleep apnea, snoring, and temporomandibular joint and musculoskeletal disorders of the jaw are only adjustable longitudinally, and in one dimension. Also, if the therapy has been shown to be ineffective and an adjustment of vertical or lateral positioning of the custom oral appliance is to be made, then it requires that a new custom oral appliance be fabricated in the new therapeutic position. The invention claimed here solves this problem.

Broadly, one embodiment of the present invention is a plurality of mechanical connectors and attachments made of plastic, ceramic, or metal, that convert any dental or oral appliances, dentures, dental or orthodontic retainers, and orthodontic appliances, into multipurpose, three dimensionally adjustable oral appliances for treating obstructive sleep apnea, snoring, temporomandibular joint and musculoskeletal disorders of the jaw, and for improving breathing from the mouth even when nasal passages are blocked.

There are no similar inventions to date where existing dental appliances, oral appliances, dentures, dental or orthodontic retainers, and orthodontic appliances treating dental, oral or orthodontic conditions, are made into multifunctional appliances that simultaneously treat obstructive sleep apnea, snoring and temporomandibular joint and musculoskeletal disorders of the jaws.

Currently, for patients suffering from multiple conditions, there is no consistent method of simultaneously treating multiple conditions, so the patient must treat one condition at a time. Secondly, outsourcing the manufacturing of a custom oral appliance delays treatment. Thirdly, research has proven that effective treatment for obstructive sleep apnea, snoring and temporomandibular joint and musculoskeletal disorders of the jaws requires a 3-dimensional positioning and adjustment of the jaws and there is no oral appliance that can be adjusted in x, y, and z axis, 3 dimensionally.

The claimed attachments 10 can be added onto a patient's existing dental appliance 30, such as a denture, an oral appliance, a dental or an orthodontic retainer, or an orthodontic appliance at the time of diagnosis. If multiple conditions have been diagnosed, the laboratory can build the attachments 10 as part of the appliance 30 treating the primary diagnosis. The dentist then chooses a titration connector 18 and attaches the titration connector 18 to the attachments 10 in the 3-dimensional required position for effective treatment of obstructive sleep apnea, snoring and temporomandibular joint and musculoskeletal disorders of the jaws.

Advantageously, these attachments 10 and titration connector 18 can improve breathing for patients who have restricted or obstructed breathing from their nose.

As shown in FIGS. 1-14, aspects pf the claimed invention includes the an attachment 10, a titration connector 18, an upper dental appliance 30, and a lower dental appliance 32. The upper dental appliance 30 is fitted to the patient's maxillary/upper jaw 34, while the lower dental appliance 32 is fitted to the patient's mandible/lower jaw 36.

The attachment 10 includes an attachment base 12 that may be secured to the dental appliance 30, 32 via an adhesive, or bonding agent 40. In some embodiments, the attachment 10 may be integrally formed with the dental appliance 30, 32. An attachment neck 14 is interposed between the attachment base 12 and an attachment head 16. The neck 14 presents a constriction between the attachment base 12 and the attachment head 16.

The titration connector 18 is formed as a flat plate having a first end and a second end. A titration connector opening 20 is dimensioned to fit over and be retained on the attachment head 16 so that the titration connector opening 20 is positioned about the neck 14. The titration connector opening 20 has a defined center point 22 (CP) which are defined at a predetermined vertical separation dimension (CPV) along the titration connector 18 and a predetermined horizontal dimension (anterior-posterior) (CPAP) 26. In the embodiment shown in reference to FIGS. 6-9, the CPAP 26 is zero.

In the embodiment shown in reference to FIGS. 11-14, the titration connector 18 may be formed as an L-shaped plate, in which one titration connector opening 20 is disposed on the base of the L and a second titration connector opening 20 is positioned on the leg of the titration connector 18. In this embodiment, the center points 22 of titration connector openings 20 have a CPV 24 corresponding to the desired vertical separation and a desired CPAP 26, representing a desired anterior/posterior offset. As will be appreciated, the orientation of the L-shaped plate, when applied to the attachments 10 determine whether the CPAP 26 will have an anterior or a posterior alignment. As seen in reference to FIG. 15, a notch 19 may be defined in the connector 18 to facilitate positioning of the connector 18 on the attachment.

In one embodiment, at least one attachment 10 is firmly affixed to each side of the maxillary/upper jaw dental appliance 30 in the midpoint area of canine 38 (or any accessible posterior tooth), (after the area has been cleaned and primed with an appliance surface cleanser and primer,) using a dental bonding cement, bonding primer, bonding agent, or light curing composite using curing light (herein referred to as "bonding element" 40.)

The dentist positions a mandibular/lower jaw dental appliance 32, into the therapeutic position while the patient is wearing the mandibular/lower jaw dental appliance 32 and marks the midpoint of the tooth area on either side that vertically aligns with the maxillary/upper jaw canine 38 (or any accessible posterior tooth where the attachment 10 was bonded) area 34.

Attachment 10 is then firmly affixed onto the marked areas after the areas have been cleaned and primed with appliance surface cleanser and primer, using the dental bonding element 40. Vertical distance between attachments 10 in the canine 38 (or any accessible posterior tooth) area and attachment 10 on each side is measured and appropriate connectors 18 are used to connect attachments 10 on each side of the maxillary/upper jaw dental appliance 30 holding the jaws together at the desired therapeutic position.

Figure 6:
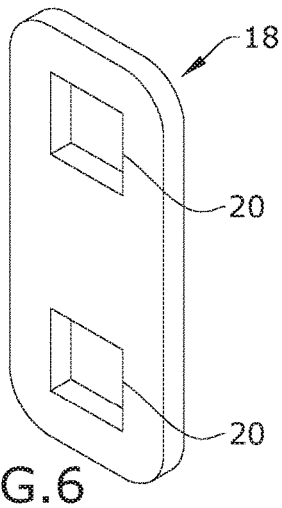
FIG. 6 is a perspective view of an invention component 18 titration connector with a zero 30 titration vertical dimension (V) (CPV-4 mm)
Figure 7:
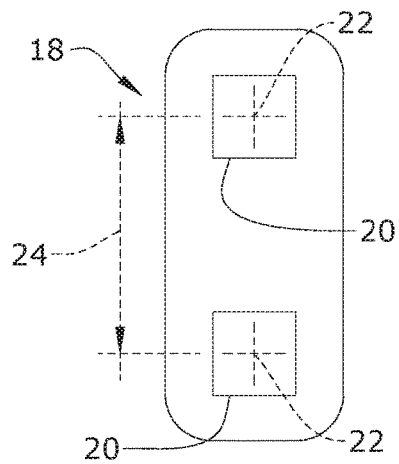
FIG. 7 is a front view of an invention component 18 titration connector with a zero 30 titration vertical dimension (V) (CPV-4 mm)
Figure 8:
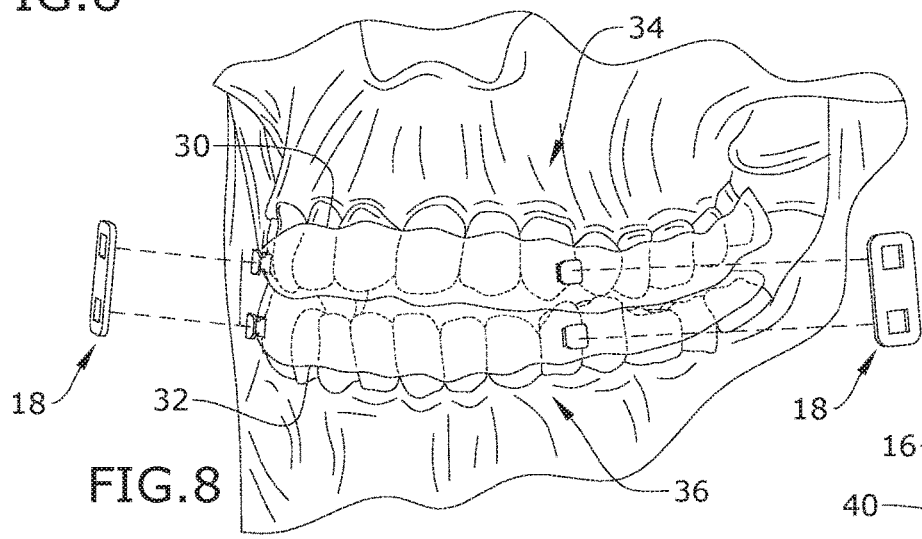
FIG. 8 is an exploded view of an invention component 18 titration connector with a zero 30 titration vertical dimension (V) (CPV-4 mm) demonstrating the attachment phase of the invention in an exemplary configuration.
Figure 9:
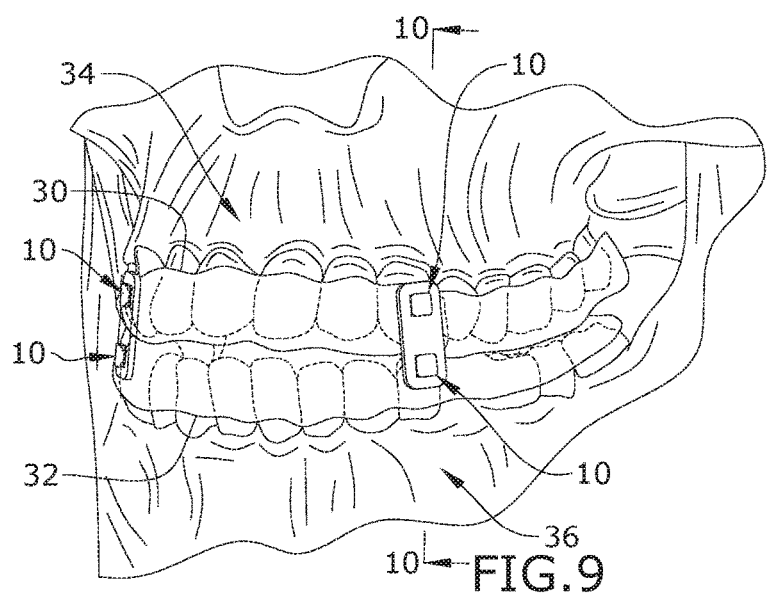
FIG. 9 is an exploded view of an invention component 18 titration connector with a zero 30 titration vertical dimension (V) (CPV-4 mm) demonstrated post attachment phase of the invention in an exemplary configuration.
Figure 10:
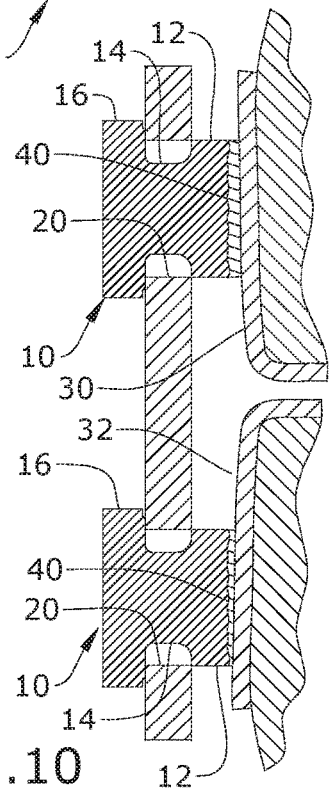
FIG. 10 is a section view of the invention taken along line 10-10 in FIG. 9.

Adjustment/repositioning/titration connectors 18 are available in a range of heights, lengths, shapes, and thickness that allow for 3-dimensional realignment of attachments 10 on each side of maxillary/upper jaw dental appliance 30, and/or on each side of mandibular/lower jaw dental appliance 32. For example, FIGS. 11-12 show one embodiment of the titration connectors 18 with a non-zero horizontal dimension, while FIGS. 6-7 show an embodiment of titration connectors 18 with zero horizontal dimension.

Figure 15:
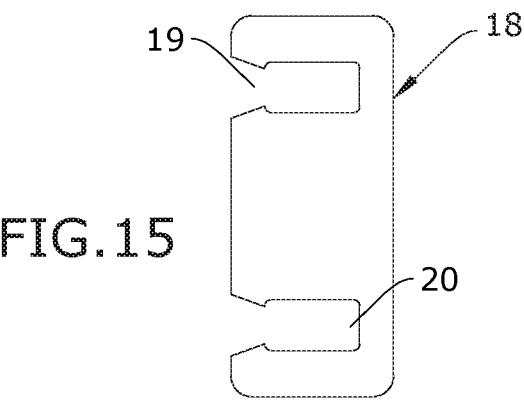
FIG. 15 is a front view of an alternate embodiment of the invention.
Figure 16:
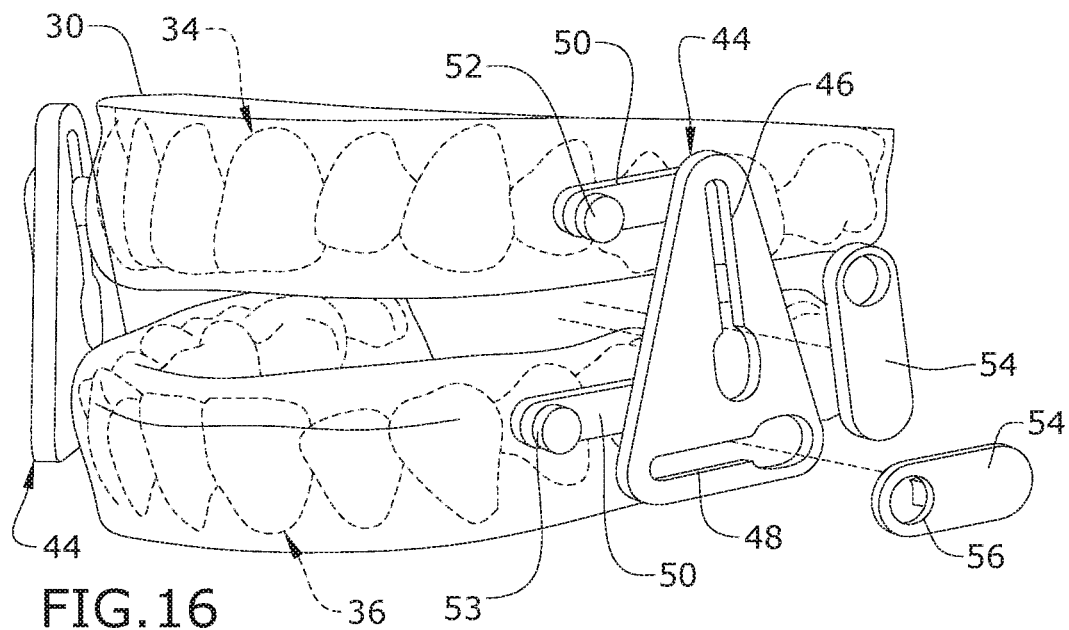
FIG. 16 is an exploded view of an alternate embodiment of the invention.
Figure 17:
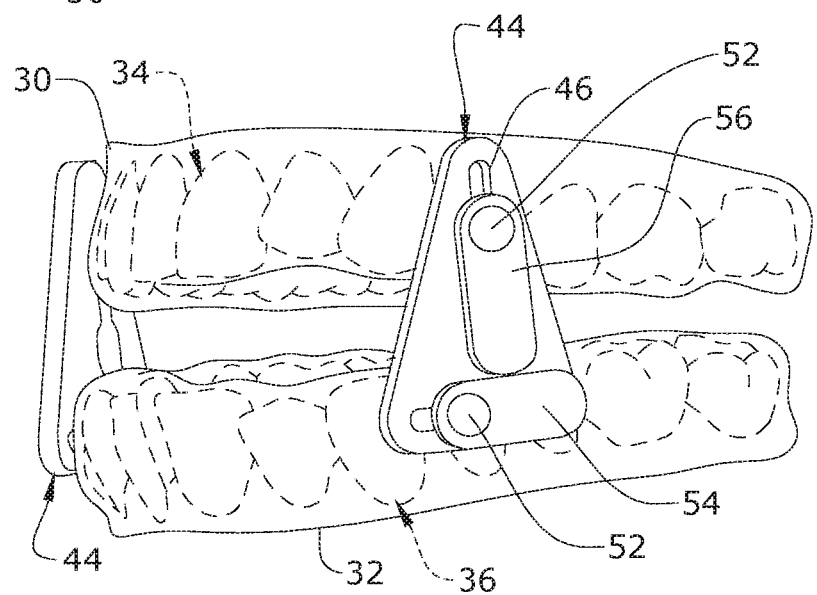
FIG. 17 is a perspective view of an alternate embodiment of the invention.

Alternative embodiments of connectors are shown in FIGS. 15-17. The components of this embodiment may include an attachment 50, a titration connector 42, and a locking element 54. One attachment 50 is affixed to an upper appliance 32 fitted to the patient's maxillary/upper jaw 35 and another attachment 50 is attached to the mandibular/lower jaw. The attachment 50 includes a head 52 at a distal end thereof and a constriction 53 defined intermediate the head 52 and a base of the attachment 50.

The titration connector 44 includes a first keyed slot 46 with an origin of the key slot 46 dimensioned to receive the head 52 and a vertical extension of the keyed slot 46 dimensioned to receive the constriction 53. In the embodiment shown, the titration connector 44 may also include a second keyed slot 48, with a horizontal extension of the second keyed slot 48 extending from the origin of the second keyed slot 48. In other embodiments, the second keyed slot 48 and the first keyed slot 46 may share a common origin.

The locking element 54 is an elongate plate having a first end and a second end. A locking aperture 56 is defined at the first end. The second end has an arcuate edge surface. The locking aperture 56 is dimensioned to be received over the head 52 and received in the constriction 53 so that the attachment 50 is retained at a desired position.

As can be seen from the alternative embodiment, the connectors 44 can be of any suitable shape, size, and configuration to treat the orthodontic issues at hand.

In operation, the dentist or dental technician firmly affixes attachments 50 to the dental appliance 32, the midpoint of canine 38 (or any accessible posterior tooth) areas on either side of the maxillary/upper jaw part of the dental appliance 30 proximal to the canine 38 (or any accessible posterior tooth) area. The dentist or dental technician then positions the mandible/lower jaw 36 with the patient wearing the mandibular/lower jaw part of the dental appliance 32 and marks on either side of it, the areas of midpoint of the tooth part that vertically align with the attachments 50 on the maxillary/upper jaw part of the dental appliance 30. The dentist measures on each side, the vertical distance between the maxillary and mandibular attachments 50 is adjusted along the vertical slot 46 to the appropriate height for each side and selects locking elements 54 of the appropriate length such that, when applied to the attachments 50, the second end of the vertical locking element 54 is in abutment with a side of the horizontal locking element 54. The arcuate edge allows the locking element 54 to be rotated into position about the constriction 53. As will be appreciated, adjustment in the anterior/posterior axis may be facilitated by positioning of the attachment 50 applied to the lower appliance 32 at the desired position and applying the locking element 54, preferably before making the vertical adjustment.

For example, for the treatment of obstructive sleep apnea and snoring, the patient just before going to sleep, wears the maxillary 30 and mandibular dental appliance 32 and moves the lower jaw until such time the attachments 50 on both sides vertically align within the slot 46 and then connects/snaps the locking element 54 onto the heads 52 of the attachments 50. By doing so, the jaw is positioned and held together at a desired therapeutic position, converting the dental appliances 30, 32 into oral appliances that also treat obstructive sleep apnea and snoring. For discontinuing treatment upon awakening or for any reason, the patient simply detaches/snaps off the connectors 18 and the jaws can then move independently.

Similarly, for the treatment of temporomandibular joint and musculoskeletal disorders of the jaw, the patient wears the maxillary and mandibular dental appliances 30, 32 and moves the lower jaw until such time the attachments 10 on both sides vertically align and then connects/snaps the connectors 18 onto the corresponding attachments 10. By doing so, the jaw is positioned and held together at a desired therapeutic position, converting the dental appliances into oral appliances that also treat temporomandibular joint and musculoskeletal disorders of the jaws. For discontinuing treatment for any reason, the patient simply detaches/snap off the connectors 18 and the jaws can move independently.

If that therapeutic position of the lower jaw must be changed for any reason, the dentist determines the new therapeutic position and without the need to reposition the attachments 10, measures the vertical and longitudinal distances between the maxillary and mandibular attachments on each side in the new therapeutic position while the patient is wearing the maxillary and mandibular dental appliances 30, 32. He then chooses the appropriate titration connector dimensions 18 that position and hold the jaw in its new therapeutic position.

In an alternative embodiment, the oral appliances 30, 32 are manufactured with or without the attachments 10 by an automated machine such as by CAD-CAM, 3-D printing, stereo lithography, injection molding or any other automated mechanism, as can the attachments 10 and connectors 18 as well.

In each embodiment, a desired lateral offset may be obtained by positioning the constriction 14, 53 at a predetermined distance from the base 16.

In an additional embodiment, besides creating oral appliances for the treatment of obstructive sleep apnea, snoring, temporomandibular joint, and musculoskeletal disorders of the jaw, the attachments 10 and connectors 18 can improve breathing for patients who have restricted or obstructed breathing from their nose.

It should be understood, of course, that the foregoing relates to exemplary embodiments of the invention and that modifications may be made without departing from the spirit and scope of the invention as set forth in the following claims.

What is claimed is:

1. A method of treating sleep apnea and snoring in a patient by adapting a dental appliance into a multifunctional oral appliance, comprising:

affixing an attachment piece having a base at a proximal end, a head at a distal end, and a constriction intermediate the base and the head to each of a left side and a right side of a maxillary dental appliance and a mandibular dental appliance, wherein the base of each attachment piece is affixed at a midpoint overlying the facial buccal surface of one of a canine or a pre-molar of the maxilla on each of the left side and the right side of the maxillary dental appliance and a midpoint overlying the facial buccal surface of a corresponding canine or pre-molar of the mandible on each of the left side and the right side of the mandibular dental appliance, respectively; and providing a titration connector that is a rigid plate with a plurality of titration connector openings dimensioned to be received in the constriction and removably retained by the head of one of the attachment pieces in a snap fit configuration; and applying the titration connector directly between the attachment piece of the maxillary dental appliance and the mandibular dental appliance on the left or right side using the snap fit configuration of the plurality of titration connector openings onto the maxillary attachment piece and mandibular attachment piece, respectively, such that the titration connector is substantially perpendicular to an occlusal surface of the teeth;

improving restricted or obstructed breathing by wearing the multifunctional oral appliance with the applied titration connector during sleep, which holds the maxilla and mandible in a therapeutic position.

2. The method of claim 1, further comprising:

disposing the plurality of titration connector openings at a predetermined vertical separation dimension (CPV).

3. The method of claim 1, further comprising:

disposing the plurality of titration connector openings on the titration connector at a predetermined anterior-posterior dimension (CPAP).

4. The method of claim 1, further comprising:

providing a desired lateral offset to the titration connector by positioning the constriction of at least one of the attachment pieces at a predetermined distance from the base of the at least one of the attachment pieces.

* * * * *